United States Patent [19]

Nick et al.

[11] Patent Number: 4,699,792
[45] Date of Patent: Oct. 13, 1987

[54] SELF-ADHESIVE PLASTER CONTAINING MEDICATION

[75] Inventors: Erich Nick, Pinneberg; Günter Guse, Hamburg; Bodo Asmussen, Ammerbek, all of Fed. Rep. of Germany

[73] Assignee: Beiersdorf AG, Hamburg, Fed. Rep. of Germany

[21] Appl. No.: 745,169

[22] Filed: Jun. 17, 1985

[30] Foreign Application Priority Data

Jun. 23, 1984 [DE] Fed. Rep. of Germany ....... 3423328

[51] Int. Cl.$^4$ ..................... A61F 13/02; A61L 15/03; A61L 15/06
[52] U.S. Cl. .................................. 424/446; 424/449; 604/896; 604/897; 604/307; 128/156; 428/355
[58] Field of Search ...................... 424/16, 19, 20, 21, 424/26, 27, 28, 78, 83, 443, 446, 449; 604/897, 896, 304, 307; 128/156; 156/327, 332, 334; 428/354, 355, 356

[56] References Cited

U.S. PATENT DOCUMENTS 4,390,027 6/1983 Alani et al. ......................... 604/307

FOREIGN PATENT DOCUMENTS 2743979 4/1979 Fed. Rep. of Germany .
3202775 3/1983 Fed. Rep. of Germany ........ 424/28

*Primary Examiner*—John Kight
*Assistant Examiner*—Nathan M. Nutter
*Attorney, Agent, or Firm*—John C. Smith, Jr.

[57] ABSTRACT

A self-adhesive medicinal plaster comprises a plurality of adhesive elements spaced from each other on a surface of a carrier web and a plurality of active ingredient elements, containing a medication, spaced from each other and from the active ingredient elements on the surface of the carrier web whereby the medicinal active ingredient composition is isolated from the adhesive composition.

21 Claims, 2 Drawing Figures though such a plaster is economical to produce it has serious disadvantages and has not found acceptance in practice. In particular, the interactions between the active ingredient and adhesive composition impair uniform long-term release of the active ingredient through the skin because of migration, either of the active ingredient into the adhesive composition or the plasticizer or plasticizer-like substance into the active ingredient element, depending on external influences such as temperature and moisture. Such a plaster cannot fulfill the strict regulations of governmental registration as a drug especially in respect of the required storage stability under possibly adverse conditions during which migration phenomena may take place over a prolonged period.

SELF-ADHESIVE PLASTER CONTAINING MEDICATION

FIELD OF THE INVENTION

This invention relates to a self-adhesive plaster with medicinal active ingredient elements and adhesive elements spaced from each other on a carrier for transdermal application.

BACKGROUND OF THE INVENTION

Plasters for transdermal application of medicinal active ingredients are known. Transdermal plasters are commercially available and are described in a large number of publications and patents.

In one type of transdermal plaster the medicinal active ingredients are arranged in a reservoir which is shielded from the skin with a control membrane which releases a controlled amount of active ingredient onto the skin through this membrane. A disadvantage of this arrangement is that the active ingredient, reservoir constituents and membrane must be carefully matched with one another, and consequently this system cannot be employed for all medicinal active ingredients. In addition, the production of such a plaster is expensive due to the complicated assembly of the parts.

In another type of transdermal plaster the medicinal active ingredient is incorporated into the adhesive composition of the plaster. In this case also, it is necessary for the active ingredient and adhesive composition to be carefully matched with one another. Although these systems are simpler and more economical to produce, they unavoidably result in interactions between the active ingredient and adhesive especially since as a general rule adhesives do not consist of defined individual constituents but are diverse mixtures.

German Offenlegungsschrift No. 3,202,775 describes an adhesive plaster for transdermal application of an active ingredient in which the active ingredient is printed onto the adhesive surface of the plaster in the form of separate spaced elements. Although such a plaster is economical to produce it has serious disadvantages and has not found acceptance in practice. In particular, the interactions between the active ingredient and adhesive composition impair uniform long-term release of the active ingredient through the skin because of migration, either of the active ingredient into the adhesive composition or the plasticizer or plasticizer-like substance into the active ingredient element, depending on external influences such as temperature and moisture. Such a plaster cannot fulfill the strict regulations of governmental registration as a drug especially in respect of the required storage stability under possibly adverse conditions during which migration phenomena may take place over a prolonged period.

An object of the present invention is, accordingly, to provide a medicated self-adhesive plaster for transdermal application which does not have, or has only to a substantially lesser degree, the above-mentioned disadvantages of the prior art. In particular, a plaster is provided which on the one hand can be produced economically and on the other hand is free from problems of migration of adhesives into the medicinal active ingredient and vice versa, and in addition, as far as possible, avoids any type of interaction between the two components.

SUMMARY OF THE INVENTION

The invention, accordingly, relates to a self-adhesive plaster with separate active ingredient elements on a carrier for transdermal application which is characterized in that adhesive elements are arranged spatially separate from the active ingredient elements on the carrier, the adhesive elements consisting of adhesive systems which can be processed as a dispersion, plastisol or organisol, and both the adhesive elements and the active ingredient elements being approximately cap-shaped and adhering to the carrier by their base.

It is particularly advantageous for the apex of the medicinal active ingredient and adhesive elements to have about the same height in relation to the carrier. A uniformly good contact of both types of elements to the surface of the skin is thereby achieved.

The plaster, according to the invention, is thus free from interaction between the medicated active ingredient and adhesive. The resulting advantages are, in particular, that adhesives of the dispersion-type and the like, which are known per se, can be used as the adhesive and that, on the other hand, the medicated active ingredient can be processed with suitable pharmaceutical auxiliaries which are used for fixing to the carrier, according to the invention, and for optimum diffusion of the active ingredient into the skin. It is therefore no longer necessary to develop a formulation of the adhesive to suit the particular medicinal active ingredient or, conversely, a formulation of the active ingredient to suit the adhesive. Rather, an exceptionally variable system results with which medicinal active ingredients of the most diverse types may be used for transdermal application.

Advantageously, both the adhesive elements and the medicinal active ingredient elements are each applied from dispersions with a high solids content by a printing process. Suitable printing processes are gravure printing processes and, in particular, screen printing processes which are distinguished by single handling and exceptional economy with precise arrangement of the elements on the carrier web.

The adhesive elements and the medicinal active ingredient elements are preferably arranged in a regular pattern due to the geometry of the screen printing devices. The caps preferably have a base diameter of up to about 5000 μm, in particular 200–500 μm. If desired, however, it is possible to produce larger caps.

Because of the spatial separation of the active ingredient and adhesive the adhesive can be any adhesive which is known per se and which does not irritate the skin and which can be processed as described above. Suitable adhesives are, inter alia, rubber, polyacrylic acid esters and polyisobutylene, if appropriate, together with tackifying resins. These adhesives are advantageously processed from aqueous, concentrated, thixotropic dispersions of adhesives, the solids content preferably being 55–65% by weight. Suitable examples are adhesives based on methyl acrylic acid esters with alkyl radicals of 4–18 carbon atoms, such as butyl acrylate, ethylhexyl acrylate or stearyl acrylate, cross-linked or noncross-linked, it being possible to effect cross-linking, if appropriate, by electron beam radiation.

The rotary screen printing process uses a rotating weldless, drum-shaped and perforated rotary screen. In the inner jacket, a mechanically or magnetically held round-edged or square doctor blade forces the dispersion into the drum through the perforations of the screen wall onto the carrier web. The carrier web passes the drum at a speed corresponding to the peripheral speed of the rotating screen drum driven by a back-pressure roller against the outer cover of the screen drum. To produce the plasters according to the invention, two synchronously running screen printing units connected in series, which place the adhesive elements and then the active ingredient elements exactly alongside one another in accordance with the whole geometry of the screens, are used in a suitable manner. The size and dosage of the microsize areas of adhesive and active ingredient which form as caps can be accurately determined by the diameter of the screen perforations and the wall thicknss of the screen. The number of possibilities of the arrangement is unlimited, and the arrangement can be selected as desired. There is thus the additional economic advantage that the adhesive formulation and active ingredient formulation can be applied to the carrier web in a production line with a high dosage accuracy.

The dispersions should be gelatinous to paste-like and, after drying, form an elastic film, for example, by addition of polvinyl alcohol, polyvinyl pyrrolidone, water-soluble cellulose derivatives or other more or less water-soluble film-forming agents. Microencapsulated substances can also be processed via the dispersion.

It is furthermore possible to apply membrane-forming substances separately in the production line, to accurately match the active ingredient, by including another screen printing unit without interfering with the adhesive.

If electron-beam cross-linking is to be carried out, this is advantageously effected after application of the adhesive and before application of the medicated active ingredient without interrupting the production line.

The coating is then advantageously dried in a hot-air canal or by infrared or high-frequency radiation.

Possible carrier webs are, in particular, diffusion-tight films. Particularly suitable carriers are those to which the adhesive and active ingredient formulation adhere without auxiliary materials. If appropriate, the surface of the carrier can also be additionally treated, for example, by corona discharge or coating with an adhesion promoter which, as a primer, effects anchoring of the active ingredient and adhesive elements.

A large number of medicinal active ingredients which are suitable for transdermal application are known. Thus, European Published Specification No. 72,251 describes a large number of such active ingredients. The following are examples:
Antihypertensive agents
Antihypotensive agents
Vasodilators
β-Blockers
Calcium antagonists
Antiemetic agents
Antitussive agents
Sedatives
Analgesics
Psychotropic agents
Antiasthmatic agents
Antirheumatic agents
Antiarythmic agents
Antihistamines
Hormones
Antibiotics
Cytostatics.

BRIEF DESCRIPTION OF THE DRAWINGS

The features and advantages of the present invention will become more clearly appreciated from the following description taken in conjunction with the accompanying drawings in which.

DETAILED DESCRIPTION OF THE PREFERRED EMBODIMENTS

Figure 1:
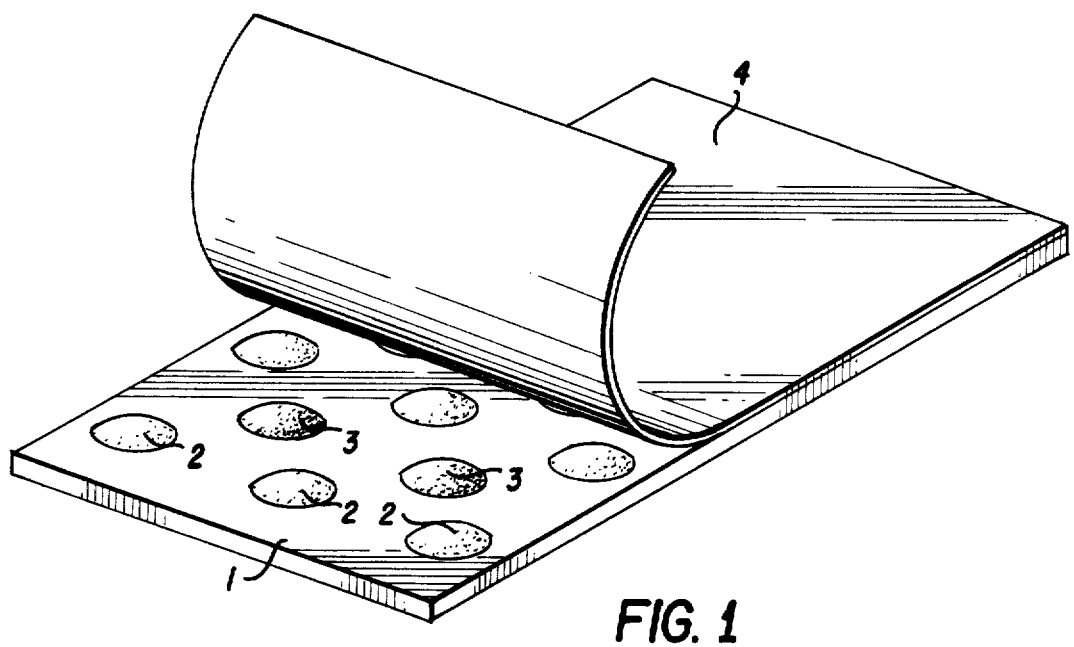
FIG. 1 is a perspective view of one embodiment of the plaster of the present invention.

In FIG. 1, cap-shaped adhesive elements 2 and medicinal active ingredient elements 3 are located on a surface of a carrier web 1. A releasable cover 4 extends over the active ingredient and adhesive elements and is releasably retained by the adhesive elements. The cover 4 preferably has an adhesive-repellent finish on the side facing the adhesive elements 2 and active ingredient elements 3, if the cover 4 is not itself already adhesive-repellent.

Figure 2:
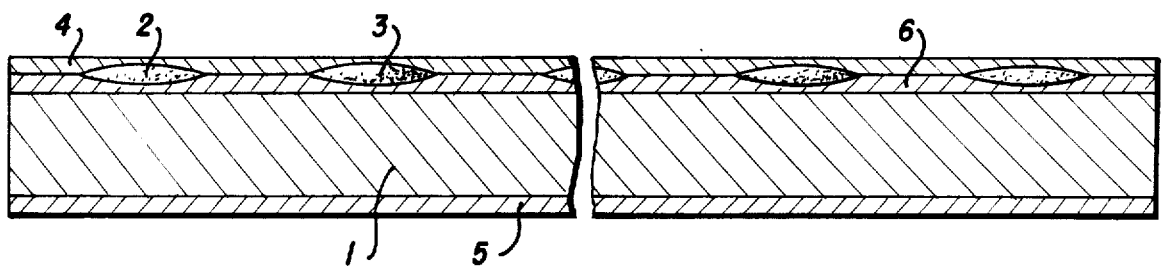
FIG. 2 is a cross-sectional view of a second embodiment of the plaster of the present invention.

FIG. 2 shows a variant of the FIG. 1 embodiment with the carrier web 1, adhesive composition elements 2 and active ingredient elements 3 embedded in an adhesive promoter 6 and covered with a releasable cover 4. On the underside of the carrier 1 is a covering lacquer 5 which can consist of a lacquer coating or a metal layer produced by vapor deposition.

The following is an example of a specific embodiment of the present invention:

EXAMPLE

A.

Preparation of a medicated active ingredient formulation 27.35 parts by weight of hydroxypropylmethylcellulose (Pharmacoat 603) are stirred into a cold mixture of 30 parts by weight of isopropanol, 30 parts by weight of water and 8.20 parts by weight of 1,2-propylene glycol. The mixture is warmed to 50° C., with continuous stirring, until a clear solution has formed. 4.45 parts by weight of micronized 2-methyl-4-chloro-6-methoxy-5-(2-imidazoline-2-yl)-amino-pyrimidine (Moxonidin) are carefully mixed into said solution.

B.

Preparation of an adhesive formulation 100 parts by weight of a commercially available aqueous polymer dispersion based on acrylic acid ester (Acronal 80 D) are thicknened to a viscosity of about 200 Pas by addition of 4 parts by weight of a 16% strength ammoniacal-aqueous solution of a polyacrylic acid (Collacral P).

C.

Printing Operation

A polyethylene terephthalate (Hostaphan RN 15) film 15 μm thick, which on one side is aluminized and lacquered the color of skin, is coated with the medicinal active ingredient formulation by a first rotating screen printing unit at a web speed of 20 m/minute. A perforated cylinder which produces rows of medicinal active ingredient elements in the longitudinal direction of the web is used. Each element has a base diameter of about 400 μm; the distance between the elements being about 100 μm in the longitudinal direction of the web and about 600 μm in the transverse direction. The amount applied is regulated via adjustment of the doctor blade so that cap-shaped elements are formed which, in the dried state, have a height of about 160 μm. This corresponds to about 25 g of medicated active ingredient formulation per m² of the carrier web. Drying is carried out at about 70° C. in a warm-air canal 6 m in length.

A second rotating screen printing unit of the same type then prints rows of elements of the adhesive formulation on the carrier web between the dried rows of elements containing the medicinal active ingredient. Thus, the amount of active ingredient formulation applied to a predetermined area of the carrier web is controlled by the element size and height. The second printing is followed by another drying zone of the type described above. The carrier web with the adhesive and medicated active ingredient elements is then passed through a laminating unit in which the web is covered with a releasable protective film, for example, a polyethylene terephthalate film 100 μm thick (Hostaphan RN 100), which is aluminized and siliconized on one side.

D.

Fabrication

The dried and covered web which has been printed twice is now divided into individual plasters of any desired size, depending on the desired doses of medicinal active ingredient. If, for example, a size of 25 cm³ is chosen, this has in each case about 5000 elements of medicinal active ingredient and adhesive, the active ingredient content being about 7 mg of 2-methyl-4-chloro-6-methoxy-5-(2-imidazolin-2-yl)-amino-pyramidine (Moxonidin). These plasters are sealed individually in a diffusion-tight primary packing material, for example, a flat bag of polyethylene/aluminum/paper laminated material.

It will be appreciated that various arrangements of the above-disclosed arrangement are possible without departing from the spirit of the present invention.

What is claimed is:

1. A self-adhesive transdermal medicinal plaster in which the medication is isolated from the adhesive, comprising:
   (a) an impermeable carrier web;
   (b) a plurality of adhesive elements spaced from each other at predetermined locations on a surface of said carrier web; and
   (c) a plurality of active ingredient elements, containing at least one transdermal medication, spaced from each other and from said active ingredient elements at predetermined locations on said surface of said carrier web;
   (d) said active ingredient elements being disposed between a plurality of said adhesive elements and said adhesive elements being disposed between a plurality of said active ingredient elements on said surface of said carrier web, and the height of said active ingredient elements and the height of said adhesive elements on said carrier web being about the same to assure, when said plaster is applied to the skin, uniformly good contact of both said active ingredient and adhesive elements with the surface of the skin.

2. A self-adhesive medicinal plaster according to claim 5 wherein each of said adhesive elements and each of said medicinal active ingredient elements are approximately cap-shaped and adhere at its base to said surface of said carrier web.

3. A self-adhesive medicinal plaster according to claim 2 wherein the apexes of said medicinal active ingredient elements and said adhesive elements are approximately the same height relative to said surface of said carrier web.

4. A self-adhesive medicinal plaster according to claim 5 wherein each of said medicinal active ingredient elements is surrounded by a plurality of said adhesive elements and each of said adhesive elements is surrounded by a plurality of said medicinal active ingredient elements.

5. A self-adhesive medicinal plaster according to claim 4 wherein said medicinal active ingredient elements and adhesive elements have a base dimension of up to about 5000 μm.

6. A self-adhesive medicinal plaster according to claim 5 wherein the base dimension of said medicinal active ingredient elements and said adhesive elements is between 200 and 1500 μm.

7. A self-adhesive medicinal plaster according to claim 5 wherein the adhesive of said adhesive elements is selected from the group consisting of rubber, a polyacrylic acid ester, polyisobutylene and mixtures thereof with tackifying resins.

8. A self-adhesive medicinal plaster according to claim 5 wherein said medicinal active ingredient further comprises at least one pharmaceutical auxiliary or excipient.

9. A self-adhesive medicinal plaster according to claim 5 further comprising an adhesion promoter coating on said surface of said carrier web for promoting adhesion of said medicinal active ingredient elements and said adhesive elements to said carrier web.

10. A self-adhesive medicinal plaster according to claim 5 further comprising a film covering the surface of said carrier web opposite said surface supporting said medicinal active ingredient and adhesive elements, said film being selected from the group consisting of lacquer and metal.

11. A self-adhesive medicinal plaster according to claim 5 wherein said active ingredient elements comprise 2-methyl-4-chloro-6-methoxy-5-(2-imidazolin-2-yl)-amino-pyramidine.

12. A self-adhesive medicinal plaster according to claim 5 wherein a portion of said active ingredient elements comprise one type of medicinal composition and the remainder of said active ingredient elements comprise a different medicinal composition.

13. A self-adhesive medicinal plaster according to claim 5 further comprising a releasable cover web covering said surface of said carrier web including said medicinal active ingredient and adhesive elements.

14. A method of making a self-adhesive transdermal medicinal plaster in which the medication is isolated from the adhesive, comprising applying, by gravure printing processes, a dispersion, plastisol or organisol of an adhesive having a high solids content and a dispersion of at least one transdermal medication having a high solids content at spaced locations on one surface of an impermeable carrier web and drying said adhesive and said medication to form a plurality of adhesive elements and a plurality of transdermal medicinal active ingredient elements spaced from each other at predetermined locations on said surface of said carrier web, said elements being arranged such that each of said medicinal active ingredient elements is disposed between a plurality of said adhesive elements and each of said adhesive elements is disposed between a plurality of said medicinal active ingredient elements, the amount of dispersion, plastisol or organisol of said adhesive and the amount of said dispersion of at least one medication applied to said carrier web being such that the height of the resultant adhesive elements and the height of the resultant active ingredient elements on said carrier web are about the same to assure, when said plaster is applied to skin, uniformly good contact of both said adhesive and active ingredient elements with the surface of the skin.

15. A method of making a self-adhesive plaster according to claim 19 wherein said gravure printing processes are screen printing processes.

16. A method of making a self-adhesive plaster according to claim 19 wherein said adhesive applied to said carrier web is an aqueous, thixotropic dispersion of adhesive with a solids content of 55-65% by weight.

17. A method of making a self-adhesive plaster according to claim 19 comprising first applying said adhesive to said carrier web, drying said adhesive to form said plurality of adhesive elements, and cross-linking the composition of said adhesive elements and then applying said medication to form said medicinal active ingredient elements and drying said medicated active ingredient elements.

18. A method of making a self-adhesive plaster according to claim 17 wherein said cross-linking of said adhesive elements is by means of electron beam radiation.

19. A method of making a self-adhesive plaster according to claim 14 wherein the amount of dispersion, plastisol or organisol of said adhesive and the amount of said dispersion of at least one medication applied by said gravure printing processes, respectively, provides adhesive elements and medicinal active ingredient elements respectively having a maximum base dimension of about 5000 μm.

20. A method of making a self-adhesive plaster according to claim 19 wherein said dispersion, plastisol or organisol of an adhesive having a high solids content is first applied by said gravure printing process to said surface of said carrier web and said adhesive is dried to form said plurality of adhesive elements on said carrier web and then said dispersion of at least one medication having a high solids content is applied by a further gravure printing process at spaced locations and spaced from said adhesive elements on said surface of said carrier web and said adhesive is dried to form said plurality of adhesive elements.

21. A method of making a self-adhesive plaster according to claim 19 wherein the amount of dispersion, plastisol or organisol of said adhesive and the amount of said dispersion of at least one medication applied by said gravure printing processes, respectively, provides adhesive elements and medicinal active ingredient elements respectivly having a base dimension between 200 and 1500 μm.

* * * * *

UNITED STATES PATENT AND TRADEMARK OFFICE
CERTIFICATE OF CORRECTION

PATENT NO. : 4,699,792
DATED : October 13, 1987
INVENTOR(S) : Erich Nick, Günter Guse and Bodo Asmussen It is certified that error appears in the above–identified patent and that said Letters Patent are hereby corrected as shown below:

Column 6: Line 15 should read:

"claim 1 wherein said medicinal active ingredient ele-"

Signed and Sealed this

Fifth Day of July, 1988

Attest:

DONALD J. QUIGG

Attesting Officer

Commissioner of Patents and Trademarks